United States Patent [19]
Noritake et al.

[11] Patent Number: 5,609,675
[45] Date of Patent: Mar. 11, 1997

[54] INORGANIC COMPOSITION

[75] Inventors: Masaki Noritake; Shigeki Yuasa, both of Tokuyama, Japan

[73] Assignee: Tokuyama Corporation, Tokuyama, Japan

[21] Appl. No.: 496,280

[22] Filed: Jun. 30, 1995

[30] Foreign Application Priority Data

Jul. 4, 1994 [JP] Japan .................................. 6-152428

[51] Int. Cl.$^6$ .................................................. C04B 35/10
[52] U.S. Cl. ............................ 106/35; 501/123; 501/153; 501/133; 501/154
[58] Field of Search .................................. 501/123, 153, 501/133, 154; 106/35

[56] References Cited

U.S. PATENT DOCUMENTS 5,228,907  7/1993  Eppinger et al. ........................ 106/35

FOREIGN PATENT DOCUMENTS 60-11408   5/1985   Japan .
4-210609  11/1992   Japan .

*Primary Examiner*—Melissa Bonner
*Attorney, Agent, or Firm*—Sherman and Shalloway

[57] ABSTRACT

An inorganic composition comprises (A) 60 to 99% by weight of spherical inorganic oxide particles having a mean particle diameter greater than 0.1 μm but not greater than 1 μm, and (B) 40 to 1% by weight of inorganic oxide fine particles having a mean particle diameter not greater than 0.1 μm, wherein a volume of micro pores due to strongly aggregated particles having pore diameters not smaller than 0.08 μm is not greater than 0.1 cc per gram of the inorganic composition. The inorganic composition, when mixed with a polymerizable monomer and a catalyst, provides a composite useful for dental applications which has excellent surface smoothness, can be polished in a short time, exhibits improved bending strength, compressive strength, surface hardness and wear resistance and causes little wear on an antagonistic tooth.

15 Claims, 4 Drawing Sheets

— 1μm

———— 1μm

1μm

1μm

1μm 5,609,675

INORGANIC COMPOSITION

BACKGROUND OF THE INVENTION

1. Field of the Invention

The present invention relates to an inorganic composition, to a composite composition containing the above inorganic composition and, particularly, to a composite composition suited for dental applications. More specifically, the invention provides a composite composition that is suitably used for obtaining a composite cured product for dental applications, having excellent wear resistance, smoothness and mechanical strength.

2. Prior Art

A composite composition such as a composite restorative for dental applications has heretofore been used in a manner that a photo-initiation catalyst is added to an acrylic ester monomer liquid which is chiefly composed of a bisphenol A glycidyl methacrylate (addition product of bisphenol A and glycidyl methacrylate, hereinafter simply referred to as Bis-GMA), which is then blended with an inorganic filler in large amounts, so that the blend is cured with light in the oral cavity. Such a restorative has been widely used among the clinicians since its appearance is close to natural teeth compared with restoratives which are chiefly composed of a metal.

Such composite restoratives for dental applications can roughly be divided into two kinds. One is a dental composite restorative which has excellent mechanical strength and wear resistance by blending an inorganic composition having a relatively large particle diameter as a filler at a large ratio as disclosed in Japanese Laid-Open Patent Publication No. 197311/1991. The other one is a dental composite restorative which has excellent surface smoothness and wear resistance of antagonistic tooth by blending an inorganic composition having a relatively small particle diameter as a filler. Here, excellent wear resistance of antagonistic tooth means that the dental composite restorative that is charged and cured in the oral cavity does not cause the antagonistic tooth to be worn out by the occlusion.

However, the conventional cured products of dental composite restoratives are not capable of fully satisfying all of the above-mentioned features, i.e., mechanical strength, wear resistance, surface smoothness and wear resistance of antagonistic tooth.

SUMMARY OF THE INVENTION

The present inventors have conducted keen study concerning dental composite restoratives and, particularly, inorganic compositions as fillers that satisfy all of mechanical strength, wear resistance, surface smoothness and wear resistance of antagonistic tooth. As a result, the inventors have learned that the filling ratio of an inorganic composition in the composite composition can be further increased and the mechanical strength of the cured product can be improved by using an inorganic composition in which inorganic oxide particles having particle diameters of the order of submicrons and fine inorganic oxide particles having particle diameters of not larger than 0.1 μm are mixed and highly dispersed together. Astonishingly, furthermore, it was learned that the filling ratio of the inorganic composition in the composite composition can be increased and the mechanical strength of the cured product can be increased if fine particles of not larger than 0.1 μm, which so far did not contribute to improving the filling ratio, are highly dispersed to satisfy particular conditions.

That is, the present invention is concerned with an inorganic composition (C) which comprises (A) 60 to 99% by weight of spherical inorganic oxide particles having a mean particle diameter greater than 0.1 μm but not greater than 1 μm, and (B) 40 to 1% by weight of inorganic oxide fine particles having a mean particle diameter not greater than 0.1 μm, wherein a volume of micro pores due to strongly aggregated particles having pore diameters not smaller than 0.08 μm is not greater than 0.1 cc per gram of the inorganic composition (C).

The invention is further concerned with the above-mentioned inorganic composition (C) wherein the volume of micro pores due to strongly aggregated particles having pore diameters over a range of from 0.1 to 0.8 times as large as the mean particle diameter of the inorganic oxide fine particles (B) is not greater than 0.1 cc per gram of the inorganic composition (C).

The invention is concerned with any one of the above-mentioned inorganic compositions of which the surfaces are treated with a silane treating agent.

The invention further deals with a composite composition comprising 50 to 95% by weight of either the above-mentioned inorganic composition or the above-mentioned inorganic composition of which the surfaces are treated with %he silane treating agent, and 50 to 5% by weight of a radical-polymerizable monomer.

DETAILED DESCRIPTION OF THE INVENTION

Figure 1:
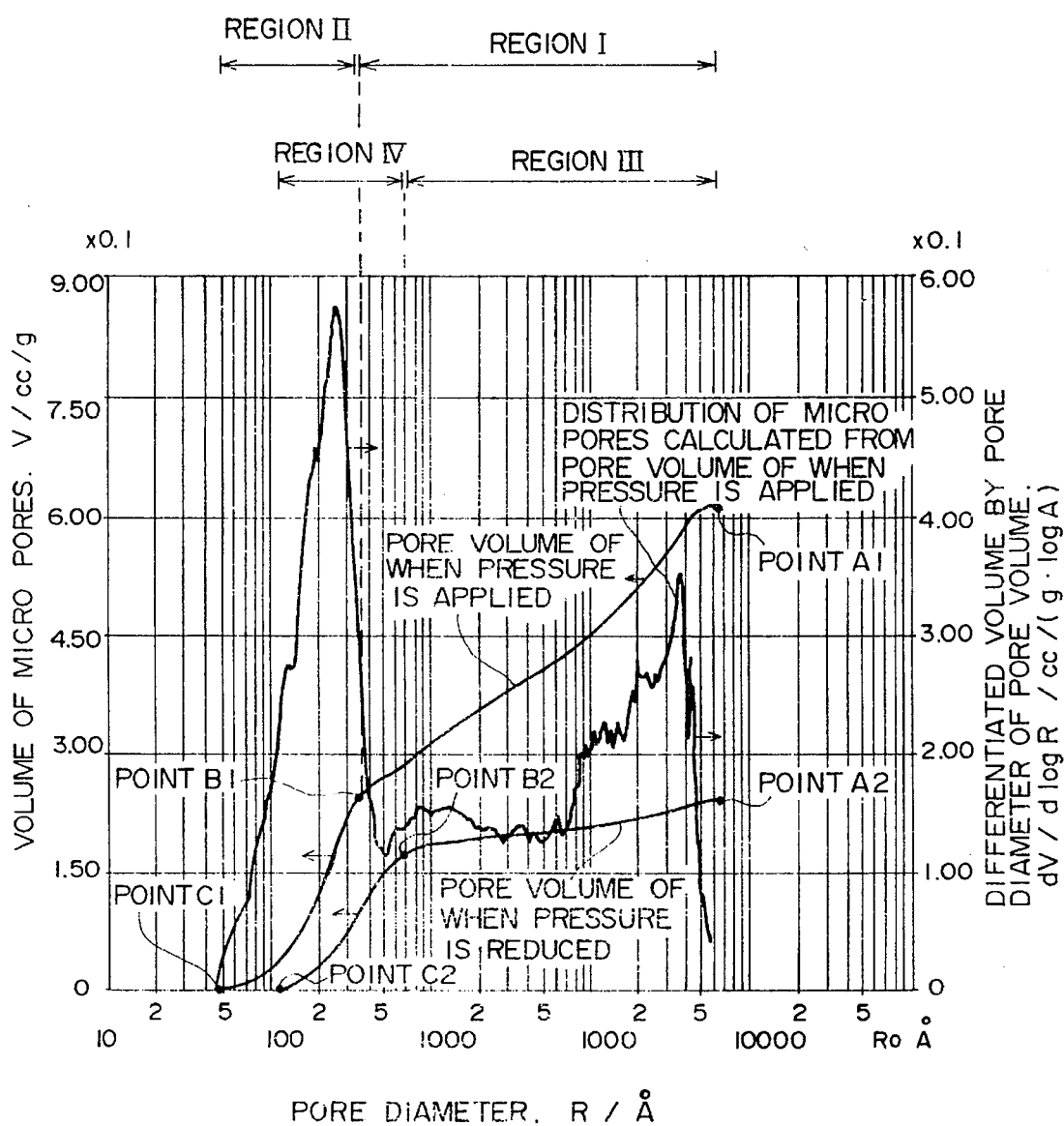
FIG. 1 is a diagram illustrating the volumes of micro pores and distributions of pore diameters of an inorganic composition used in Example 11 measured by the mercury porosimetry while increasing the pressure from atmospheric pressure through up to 203 MPa (1990 kgf/cm$^2$) and decreasing the pressure.

In the present invention, a mean volume particle diameter is employed as the mean particle diameter.

One of the components constituting the inorganic composition of the present invention comprises spherical inorganic oxide particles (A) having a mean particle diameter greater than 0.1 μm but not greater than 1 μm. Any widely known spherical inorganic oxide can be used without any particular limitation provided the mean particle diameter lies within the above-mentioned range. Preferably, the spherical inorganic oxide particles (A) comprise a siliciferous compound or an aluminiferous compound.

Concrete examples of the spherical inorganic oxide particles (A) that are usually preferably used include such spherical particles as amorphous silica, silica-zirconia, silica-titania, silica-titania-barium oxide, quartz, alumina and the like. It is also allowable to use particles of a composite oxide in which an oxide of a metal of the Group IA of periodic table is made present in a small amount in the above-mentioned inorganic oxide particles, so that there can be obtained inorganic oxide particles in a dense form when the inorganic oxide particles are being fired at high temperatures. For the dental applications, spherical particles of a composite oxide containing silica and zirconia as chief constituent components can be particularly preferably used as spherical inorganic oxide particles (A) since they have X-ray contrast property and make it possible to obtain a cured product of composite composition having excellent wear resistance.

The spherical inorganic oxide particles (A) used in the present invention need not necessarily be the inorganic oxide particles of a single group but may be mixed particles consisting of two or more groups having different mean particle diameters as is known in, for example, Japanese Patent Publication No. 10603/1991. In this case, the mean particle diameter will be a mean volume particle diameter of the mixture of particles of a plurality of groups. In this case, furthermore, there will be obtained a cured product of composite composition having excellent wear resistance, smoothness, and surface hardness, and of which the surfaces can be easily polished as has been described in the above publication.

Though there is no particular limitation in the distribution of particle diameters of starting powder of the spherical inorganic oxide particles (A), the object of the present invention can be accomplished most favorably when the starting powder has such an excellent single dispersion that a coefficient of variation in the distribution is not larger than 0.3. When the coefficient of variation is larger than 0.3, the operability of the composite composition may often decrease. Generally, therefore, it is desired that the coefficient of variation in the distribution of particle diameters is not larger than 0.3.

Even when the particle diameter and the coefficient of variation are within the above-mentioned ranges, however if the particle shape is not spherical, the effects of the invention such as smoothness of the surface of the cured product, wear resistance of antagonistic tooth and mechanical strength will not be obtained to a satisfactory degree.

The spherical inorganic oxide particles (A) can be produced by any method without any limitation provided they have particle diameters and shapes as described above. Industrially, in general, the spherical inorganic oxide particles are preferably produced by a method of hydrolyzing a metal alkoxide. To maintain surface stability of the inorganic oxide particles, furthermore, it is desired to decrease the silanol groups on the surfaces. For this purpose, the spherical inorganic oxide particles are often fired at a temperature of 500° to 1000° C. after they have been dried.

Another component constituting the inorganic composition of the present invention comprises inorganic oxide fine particles (B) having a mean particle diameter of not larger than 0.1 μm. Any widely known inorganic oxide fine particles can be used without any limitation provided their mean particle diameter lies within the above-mentioned range. Preferably, the inorganic oxide fine particles (B) comprise an oxide of an element of the Group IIIA, the Group IVA or the Group IVB of the periodic table. The inorganic oxide fine particles need not necessarily be those consisting of a single group but may be fine particles of a mixture consisting of two or more different groups provided their mean particle diameter lies within the above-mentioned range. In this case, the mean particle diameter will be a mean volume particle diameter of a mixture of a plurality of groups. As for the shapes of the particles, it is allowable to use particles of a spherical shape as well as any indeterminate shape without any limitation in the shape.

Concrete examples of the inorganic oxide fine particles (B) having particle diameters lying within the above-mentioned range that can be generally preferably used include which is a fumed silica, fumed alumina, fumed zirconia, fumed titania, amorphous silica, silica-zirconia, silica-titania, silica-titania-barium oxide, quartz, alumina, etc. It is also allowable to use fine particles of a composite oxide in which an oxide of a metal of the Group IA of periodic table is made present in a small amount in the above-mentioned inorganic oxide fine particles, so that there can be obtained inorganic oxide fine particles in a dense form when the inorganic oxide fine particles are being fired at high temperatures.

When the mean particle diameter of the inorganic oxide fine particles (B) is larger than the above-mention ed range, their blending ratio of the inorganic composition decreases in the composite composition when they are mixed into a radical-polymerizable monomer together with the spherical inorganic oxide particles (A). When the composite composition is polymerized and cured, therefore, the smoothness on the surface of the polymerized and cured product, wear resistance and mechanical strength are not obtained to a satisfactory degree.

In the inorganic composition of the present invention, it is necessary that the spherical inorganic oxide particles (A) in an amount of 60 to 99% by weight [m] and the inorganic oxide fine particles (B) in an amount of 40 to 1% by weight [n] are mixed together at a ratio of m+n=100. Preferably, the spherical inorganic oxide particles (A) in an amount of 70 to 90% by weight and the inorganic oxide fine particles (B) in an amount of 30 to 10% by weight are mixed together.

When the mixing ratio does not lie within the above-mentioned range, the effects of the present invention are little exhibited. That is, when m is smaller than 60% by weight, n becomes larger than 40% by weight, and the composite composition mixed together with the radical-polymerizable monomer loses mechanical strength after they are polymerized and cured. Conversely, even when m is not smaller than 99% by weight, the blending ratio of the inorganic composition decreases in the composite composition, and the effects of the present invention such as smoothness on the surface of the polymerized and cured product, wear resistance and mechanical strength are not exhibited to a sufficient degree.

The most important requirement in the present invention is that the volume of micro pores due to strongly aggregated particles having micro pore diameters of not smaller than 0.08 μm is not greater than 0.1 cc per gram of the inorganic composition (C).

The micro pore diameters and micro pores due to strongly aggregated particles can be measured by a mercury porosimetry. The mercury porosimetry is based upon a principle in that a fluid having a relatively large surface tension enters into micro pores having particular micro pore diameters depending upon the pressure, and is capable of measuring the distribution of micro pores present in the powder or in the porous material by gradually increasing the pressure exerted on mercury by which the sample is surrounded. Measurement can be taken by using a mercury porosimeter that has been placed in the market.

In the present invention, the micro pores due to strongly aggregated particles refer to those micro pores that exist among the particles but not inside the porous particles. The distribution of micro pores is usually measured by increasing the pressure to be not smaller than 100 MPa. So that the micro pores due to weakly aggregated particles collapse upon the infiltration of mercury of a high pressure, and it is so observed that the micro pores have extinguished since mercury is not expelled out of the micro pores when the pressure is reduced. In the distribution of micro pores obtained when the pressure is being applied by the mercury porosimetry, those micro pores that extinguish when the pressure is being reduced are referred to as micro pores due to weakly aggregated particles. Conversely, when the particles are dense and are not porous, the micro pores that do not extinguish even when the pressure is being reduced are referred to as micro pores due to strongly aggregated particles.

Here, the fact that the particles are dense and are not substantially porous can be judged relying upon whether the surface areas of the sample are in agreement with the surface areas calculated from the particle diameters observed by using a scanning electron microscope. In this case, the surface areas may be measured by the BET method, but it is also allowable to use the surface areas obtained at the time of measuring the distribution of micro pores. In general, a peak position of micro pores when the pressure is being reduced is observed to have shifted toward the side of large diameters from the position of when the pressure is applied due to a loss of pressure caused by pore surfaces. However, a correlation of peaks between when the pressure is applied and when the pressure is reduced can be easily inferred relying upon the shape of peaks, volume of micro pores and empirical rules related to the shifting amount of when the pressure is being reduced. The empirical rules referred to here are such that micro pores which are smaller than about 0.1 μm are observed as micro pores which are about 2 to 3 times as large, and micro pores which are larger than about 0.1 μm are observed as micro pores which are about 3 to 5 times as large when the pressure is being reduced. According to the present invention, the micro pore diameters are those of when the pressure is being applied and of which the values are reliable, and the volume of micro pores due to strongly aggregated particles and the extinction of peak are judged based upon the results of measurement of when the pressure is being reduced.

When it is desired to obtain a cured product of a composite composition comprising an inorganic composition and a radical-polymerizable monomer having good surface smoothness and of which the surface can be easily polished, it has been known that an inorganic composition having small particle diameters be used. When an inorganic composition having small particle diameters is used, however, the aggregated particles are little dispersed and, hence, the cured product of the composite composition loses mechanical strength. In such a case, the mechanical strength of the cured product can be effectively improved by decreasing the aggregation among the particles of the inorganic composition and by increasing dispersion property. This is obvious from the fact that when there is used an inorganic composition having particle diameters which are as large as 1 μm or more and of which the aggregation can be easily dispersed, there is obtained a cured product of a composite composition having excellent mechanical strength despite the filling ratio is the same. When the aggregation is easily dispersed, furthermore, it has been known that there can be obtained a cured product of a composite composition having excellent mechanical strength by using an inorganic composition having small particle diameters. The present inventors have conducted the study in an effort to decrease the aggregation that is a cause of reduction in the mechanical strength of the cured product of a composite composition of when there is used an inorganic composition having small particle diameters, by utilizing the above-mentioned mercury porosimetry. As a result, it was learned that there can be obtained a cured product of a composite composition having excellent mechanical strength when the volume of micro pores due to strongly aggregated particles having micro pore diameters of not smaller than 0.08 μm is not greater than 0.1 cc per gram of the inorganic composition. Though not yet clear, the following reasons can be considered. That is, micro pores due to strongly aggregated particles are not collapsed even by the infiltration of mercury of a high pressure and exist among the particles that are strongly aggregated. That is, micro pores due to strongly aggregated particles are closely related to aggregation among the particles, that is a cause of reduction in the mechanical strength of the cured product of the composite composition, and reducing the micro pores due to strongly aggregated particles makes it possible to decrease the factor that deteriorates the mechanical strength of the cured product of the composite composition. It is ideal if the micro pores due to strongly aggregated particles can be completely extinguished. Though micro pores due to strongly aggregated particles cannot be completely extinguished, however, the mechanical strength of the cured product of the composite composition can be strikingly improved as compared with that of the prior art if the volume of micro pores is decreased down to a certain level. It is further considered that the mechanical strength of the cured product of the composite composition can be effectively improved if micro pores due to strongly aggregated particles are decreased, the micro pores having relatively large pore diameters serving as a cause of destruction. In other words, it is presumed that micro pores due to strongly aggregated particles having relatively small pore diameters of not larger than 0.08 μm little serve as a factor of decreasing the mechanical strength of the cured product of the composite composition.

FIG. 1 illustrates the results of measurement of a predetermined inorganic composition (C) relying upon the mercury porosimetry. The invention will now be analyzed based upon this diagram.

As shown in FIG. 1, a change in the volume of micro pores of when the pressure is applied is divided into a region I (point A1 to point B1) where the pore diameters are large and micro pores are broadly distributed, and a region II (point B1 to C1) where the pore diameters are small and micro pores are sharply distributed. Similarly, a change in the volume of micro pores of when the pressure is reduced is divided into a region III (point A2 to point B2) and a region IV (point B2 to point C2). From the shapes of peaks, volumes of micro pores and shifting amounts of when the pressure is reduced, it will be understood that the region I is correlated to the region III, and the region II is correlated to the region IV. The volume of micro pores of about 0.39 cc/g (difference in the volume of micro pores between the point A1 and the point B1, the volume of micro pores will be found in the same manner hereinafter) in the region I where the pressure I is applied, is almost diminishing into 0.06 cc/g in the region III where the pressure is reduced. It will therefore be understood that though micro pores in the region I are basically due to weakly aggregated particles, there exist micro pores due to some strongly aggregated particles having pore diameters of not smaller than 0.08 μm in an amount of not larger than 0.06 cc/g which is the volume smaller than that of the region III. Accordingly, the measured example shown in FIG. 1 is satisfying the requirement of the inorganic composition of the present invention in that the volume of micro pores due to strongly aggregated particles having pore diameters of not smaller than 0.08 µm in the inorganic composition (C) is not greater than 0.1 cc per gram of the inorganic composition (C). It will be further understood that the micro pores appearing in the region II are not almost extinguishing in the region IV, manifesting that they are due to strongly aggregated particles.

When the volume of micro pores due to strongly aggregated particles having pore diameters of not smaller than 0.08 µm in the inorganic composition (C) is not smaller than 0.1 cc per gram of the inorganic composition, the effects of the present invention are not exhibited to a sufficient degree. When a composite composition of a radical-polymerizable monomer and the inorganic composition (C) is obtained, in particular, the product after polymerized and cured exhibits deteriorated mechanical strength.

In the inorganic composition (C), furthermore, the volume of micro pores due to strongly aggregated particles having pore diameters over a range of 0.1 to 0.8 times as large as the mean particle diameter of the inorganic oxide fine particles (B) is not greater than 0.1 cc per gram of the inorganic composition (C) in addition to that the volume of micro pores due to strongly aggregated particles having pore diameters of not smaller than 0.08 µm in the inorganic composition (C) is not greater than 0.1 cc per gram of the inorganic composition (C). In this case, further improved effects are exhibited, particularly, in regard to mechanical strength after the composite composition is polymerized and cured. Though not yet clear, the reason is considered to be as described below. In general, a peak in the pore diameter due to the primary aggregation of powder having a relatively sharp particle size distribution, appears over a range of about 0.1 to 0.8 times as large as the mean particle diameter irrespective of the strength of aggregation. When attention is given to a starting powder having a small particle diameter, in particular, the aggregation is little dispersed, and micro pores due to strongly aggregated particles can be easily observed. In such a case, from the fact that there exists almost no micro pore having a pore diameter over a range of about 0.1 to 0.8 times as large as the mean particle diameter, it is presumed that the starting powder is once completely dispersed and is completely mixed with other starting powders having different particle diameters. When the inorganic composition is used as a filler, the dispersion and mixing thereof play a very important role from the standpoint of increasing the strength of the cured product of the composite composition.

The results of measurement will now be concretely described with reference to FIG. 1. As a first example, it is now presumed that FIG. 1 is obtained as a result of measuring the inorganic composition (C) which comprises spherical inorganic oxide particles (A) having a diameter of 0.52 µm and inorganic oxide fine particles (B) having a diameter of 0.08 µm. Then, the pore diameters over a range of 0.1 to 0.8 times as large as the mean particle diameter of the inorganic oxide fine particles (B) is from 0.008 to 0.064 µm, and the volume of micro pores over this range occupies the whole volume of micro pores in the region II and about ½ of the volume of micro pores in the region I. It is, therefore, considered that the volume of micro pores due to strongly aggregated particles having diameters of from 0.008 to 0.064 consists of the whole volume of micro pores in the region IV and about ½ of the volume of micro pores in the region III, and is 0.18 cc per gram. This first example does not satisfy the requirement in that the volume of micro pores due to strongly aggregated particles having pore diameters over a range of 0.1 to 0.8 times as large as the mean particle diameter of the inorganic oxide fine particles (B) is not greater than 0.1 cc per gram of the inorganic composition (C) as measured by the mercury porosimetry, that is contemplated in the present invention.

As a second example, it is now presumed that FIG. 1 is obtained as a result of measuring the inorganic composition (C) which comprises spherical inorganic oxide particles (A) having a diameter of 0.52 µm and inorganic oxide fine particles (B) having a diameter of 0.015 µm. Then, the pore diameters over a range of 0.1 to 0.8 times as large as the mean particle diameter of the inorganic oxide fine particles (B) is from 0.0015 to 0.012 µm, and the volume of micro pores over this range occupies about ⅕ of the volume of micro pores in the region II. It is, therefore, considered that the volume of micro pores due to strongly aggregated particles having diameters over this range is about ⅕ of the volume of micro pores in the region IV, and is 0.03 cc per gram. Therefore, this second example satisfies the requirement in that the volume of micro pores due to strongly aggregated particles having pore diameters over a range of 0.1 to 0.8 times as large as the mean particle diameter of the inorganic oxide fine particles (B) is not greater than 0.1 cc per gram of the inorganic composition (C), that is contemplated in the present invention.

In practice, FIG. 1 shows the results of measurement of an inorganic composition (C) which comprises spherical inorganic oxide particles (A) having a particle diameter of 0.52 µm and inorganic oxide fine particles (B) which is a mixture of fine particles of the above-mentioned first example and fine particles of the above-mentioned second example in an equal amount on the weight basis. Therefore, the mean particle diameter of the inorganic oxide fine particles (B) is 0.048 µm, and the pore diameters over a range of 0.1 to 0.8 times as large as the above diameter is from 0.0048 to 0.038 µm. It will be obvious that the volume of micro pores over this range occupies the whole volume of micro pores in the region II and about 1/25 of the volume of micro pores in the region I. It is, therefore, considered that the volume of micro pores due to strongly aggregated particles having pore diameters over the above-mentioned range consists of the whole volume of micro pores in the region IV and about 1/25 of the volume of micro pores in the region III, and is 0.17 cc per gram. Therefore, the practically measured example shown in FIG. 1 fails to satisfy the requirement in that the volume of micro pores due to strongly aggregated particles having pore diameters over a range of 0.1 to 0.8 times as large as the mean particle diameter of the inorganic oxide fine particles (B) is not greater than 0.1 cc per gram of the inorganic composition (C).

In the inorganic composition (C), furthermore, a flow index a, an adhesive force index 1/b and a final tapping bulk density d (g/cc) can be regarded as factors that represent properties of the composition. By measuring the number of taps N, and number of taps/reduction of bulk volume N/C, these factors can be found from the following Kawakita's formula, $$(N/C)=(1/ab)+(1/a)N$$

Japanese Laid-Open Patent Publication No. 1605/1994 discloses a silica powder having good dispersion property, a flow index a of not larger than 0.4, an adhesive force index 1/b of not smaller than 10, and a final tapping bulk density d of not smaller than 0.6. When the inorganic composition (C) of the present invention is expressed by using these factors, the flow index a is not larger than 0.37, the adhesive force index 1/b is smaller than 10, and the final tapping bulk density d is not smaller than 1.0, which are favorable properties.

There is no particular limitation on the method of producing an inorganic composition (C) in which a volume of micro pores due to strongly aggregated particles having pore diameters of not smaller than 0.08 μm is not greater than 0.1 cc per gram of the inorganic composition (C), and in which a volume of micro pores due to strongly aggregated particles having pore diameters over a range of 0.1 to 0.8 times as large as the mean particle diameter of the inorganic oxide fine particles (B) is not greater than 0.1 cc per gram of the inorganic composition (C). Generally, any method can be employed provided it makes it possible to disperse the aggregated powder and to mix it to a sufficient degree.

A concrete device for effecting the dispersion and mixing can be represented, preferably, by an emulsifying and dispersion device that gives shock under super-high pressure, a nanomizer, a homogenizer and the like. By selecting the amount of samples, concentration, processing time, etc. that are suited for the respective devices, it is allowed to obtain a desired distribution of micro pores due to strongly aggregated particles. Dispersion and mixing of the inorganic composition also take place at the time of being mixed with a radical-polymerizable monomer. In this case, the distribution of micro pores due to strongly aggregated particles in the inorganic composition can be measured by extracting and removing liquid by using an organic solvent, or by heating, decomposing and removing organic materials in hydrogen at a relatively low temperature of 300° to 600° C. at which the inorganic composition is not sintered or aggregated and carbon residue is not formed, though the measurement may not be easily as a result of applying the principle for measuring the distribution of micro pores to the powder or the porous material. Conversely, it is also possible to determine an optimum mixing condition of the inorganic composition and the radical-polymerizable monomer by measuring the distribution of micro pores due to strongly aggregated particles in the inorganic composition after the organic materials have been removed by the above-mentioned method.

The inorganic composition (C) of the present invention is usually mixed into the radical-polymerizable monomer in its own form or after the surfaces thereof are treated with a silane treating agent to obtain a composite composition which can then be used by being polymerized and cured at the time of use.

Any widely known silane treating agent can be used for treating the surfaces without any limitation. Preferred examples of the silane treating agent include γ-methacryloxypropyl trimethoxysilane, hexamethyl disilazone, etc. The amount of the inorganic composition (C) treated with the silane treating agent is usually from 0.1 to 30 parts by weight per 100 parts by weight of the inorganic oxide. In treating the surfaces, furthermore, the silane treating agent is usually dissolved in a solvent such as water, ethyl alcohol or methylene chloride, and the inorganic composition is treated in this solution. The solvent is then removed.

According to the present invention, the composite composition must contain the inorganic composition (C) in an amount of 50 to 95% by weight to accomplish the object of the invention. When the content of the inorganic composition (C) is smaller than 50% by weight, the composite composition after cured exhibits inferior mechanical strength and, besides, contracts greatly during the polymerization, and cannot be used as a composite restorative for dental applications. When the content of the inorganic composition (C) is larger than 95% by weight, on the other hand, the mechanical strength decreases due to the presence of bubbles, and the surface smoothness is deteriorated, either.

There is no particular limitation on the radical-polymerizable monomer that constitutes the composite composition and any monomer can be used provided it is radical-polymerizable. The radical-polymerizable monomer is present in the composite composition in an amount of 50 to 5% by weight. There can be used any known monomer that has generally been used as a dental restorative. The most representative example is an acrylic ester radical-polymerizable monomer having an acrylic group and/or a methacrylic group.

Preferred examples include bisphenol-A diglycidyl methacrylate (hereinafter referred to as bis-GMA), methyl methacrylate, bismethacryloethoxyphenyl propane (hereinafter referred to as D-2.6E), triethylene glycol dimethacrylate (hereinafter referred to as 3G), tetramethylol triacrylate, tetramethylolmethane trimethacrylate, trimethylolethane trimethacrylate, and the like. A radical-polymerizable monomer having an urethane structure can be also preferably used. These radical-polymerizable monomers have been widely known for dental applications, and can be used alone or being mixed together depending upon the requirement.

Desirably, the present invention is concerned with an inorganic composition (C) which comprises (A) 70 to 90% by weight of spherical inorganic oxide particles composed chiefly of silica zirconia having a mean particle diameter greater than 0.1 μm but not greater than 1 μm, and (B) 30 to 10% by weight of inorganic oxide fine particles composed chiefly of at least one kind of inorganic oxide selected from the group consisting of silica, alumina, silica zirconia and silica titania having a mean particle diameter not greater than 0.1 μm, wherein a volume of micro pores due to strongly aggregated particles having pore diameters not smaller than 0.08 μm is not greater than 0.1 cc per gram of the inorganic composition (C). After cured, the composite composition which contains the above-mentioned inorganic composition exhibits very excellent surface smoothness, wear resistance and mechanical strength.

There is no particular limitation on the radical polymerization catalyst that is used in the present invention, and any widely known radical generator can be used without any limitation. The radical polymerization catalyst is present in the composite composition in a catalytic amount.

For instance, there can be favorably used organic peroxides such as benzoyl peroxide, parachlorobenzoyl peroxide and tartiary butylperoxy benzoate, azo compounds such as azobisisobutylonitryl, etc., and organic compounds such as tributyl borate.

The polymerization can also be carried out at normal temperature by using the above-mentioned organic peroxide and the amine compound in combination. Preferred examples of such an amine compound include a secondary or tartiary amine compound in which the amino group is bonded to the aryl group from the standpoint of promoting the curing.

For instance, there can be preferably used N,N'-dimethyl-p-toluidine, N,N'-dimethylaniline, N'-β-hydroxyethylaniline, and the like.

As the radical polymerization catalyst, furthermore, there can be favorably used a photo-sensitizer that generates radicals upon irradiation with light from the standpoint of improving strength of the cured product of the composite composition.

Examples of the photosensitizer for ultraviolet-rays include benzoin, benzoin methyl ether, acetoin benzophenone and the like. A photosensitizer that starts polymerizing upon the irradiation with visible light is more preferably used since it does not require the use of ultraviolet-rays that are harmful to human body. Their examples include α-diketones as benzil, camphorquinone, α-naphthyl and the like, and α-aminoacetophenones such as 2-benzil-dimethylamino-1-(4-morpholinophenyl)-butane-1-one, 2-benzil-diethylamino-1-(4-morpholinophenyl)-pentane-1-one and the like.

It is further desired to use the above-mentioned photo sensitizer in combination with a photo polymerization promotor. Examples of the photo polymerization promotor include tartiary amines such as N,N-dimethylaniline, p-dimethylaminobenzaldehyde, p-dimethylaminoacetophenone, p-dimethylaminobenzoic acid and the like, and barbituric acids such as 5-butyl barbiturate, 1-benzil-5-phenyl barbiturate and the like. These photo polymerization promoters may be used in one kind or in two more kinds in combination.

The composite composition of the present invention in which the inorganic oxide and the radical-polymerizable monomer are mixed together in a particular state exhibits, after cured, excellent surface smoothness and enables the surface to be polished within short periods of time. Compared with the cured products of the conventional composite compositions exhibiting similar surface smoothness and of which the surfaces can be easily polished, furthermore, the cured product of composite composition of the present invention exhibits strikingly improved bending strength, compressive strength, surface hardness and wear resistance which could not be obtained so far. Besides, the cured product of composite composition of the present invention causes the antagonistic tooth to be worn out very little, which is now becoming a clinical problem, and makes it possible to obtain a dental composite restorative that is very superior to those that were expected at first.

EXAMPLES

The invention will be concretely described below by way of Examples which, however, are not to limit the scope of the invention. Here, the below-mentioned methods were complied with for measuring various properties (particle diameters, coefficient of variation in the distribution of particle diameters, distribution of micro pores) of inorganic compositions including inorganic oxides dealt with in the following Examples and Comparative Examples, for preparing and curing pastes of composite compositions, and for measuring physical properties (compressive strength, bending strength, depth of wear by tooth brush, surface roughness, surface hardness) of composite compositions after cured.

(1) Particle Diameters and Coefficient of Variation in the Particle Diameters

The powder was photographed by using a scanning electron microscope (hereinafter referred to as SEM), the number of particles and the particle diameters observed within a unit visual field of the photograph were found, and a mean volume diameter of starting powder particles was found in compliance with the following relation and was regarded to be a mean particle diameter. A coefficient of variation in the particle diameters was also calculated.

In the case of a mixture consisting of two or more groups having different mean particle diameters, the mean volume particle diameter was calculated by adding and averaging mean particle diameters and amounts of addition of the individual groups.

$$\text{Mean particle diameter: } X = \sqrt[3]{\frac{\sum_{i=1}^{n} X_i^3}{n}} \quad \text{(mean volume diameter)}$$

$$\text{Coefficient of vatiation} = \frac{\sigma_{n-1}}{Y}$$

$$Y = \frac{\sum_{i=1}^{n} X_i}{n} \quad \text{(Number average diameter)}$$

$$\sigma_{n-1} = \sqrt{\frac{\sum_{i=1}^{n} (X_i - Y)^2}{n-1}}$$

where, n: number of particles abserved, $X_i$: diameter of i-th paritlce.

(2) Diameters of Micro Pores and Distribution of Micro Pores

About 0.2 g of the powder of a sufficiently dried inorganic composition was measured for its pore diameters and distribution of micro pores by using a mercury porosimeter (Porosimeter 2000 manufactured by Carlo Erba Co.).

(3) Specific Surface Area

Measured by using the Flowsobe II-2300 manufactured by Micrometrics Co. The principle of measurement was based upon the BET method.

(4) Preparation of a Paste of a Composite Composition and Curing

First, the surfaces of the inorganic composition were treated with a γ-methacryloxypropyltrimethoxysilane. On the other hand, a matrix monomer was prepared by adding a photo-curing catalyst and a polymerization promotor at predetermined ratios to the vinyl monomer. The above-mentioned inorganic composition and the matrix monomer were introduced into an agate mortar and were kneaded to a sufficient degree in a dark place to obtain a paste of a homogeneous composite composition.

The above-mentioned paste of the composite composition was poured into a form depending upon the kind of measurement, cured upon the irradiation with light to a sufficient degree, taken out from the form, submerged in the water maintained at 37° C. for 24 hours, and was then used as a sample piece.

(5) Compressive Strength

A cylindrical test piece 6 mm in diameter and 12 mm in height was fitted onto a tester (Autograph 5000D manufactured by Shimazu Mfg. Co.) and was measured for its compressive strength at a cross-head speed of 10 mm/min.

(6) Three-point Bending Strength

A square cylindrical test piece measuring 2×2×25 mm was fitted onto the tester (Autograph 5000D manufactured by Shimazu Mfg. Co.) and was measured for its three-point bending strength at a cross-head speed of 0.5 mm/min.

(7) Depth of Wear, Surface Roughness and Depth of Antagonistic Tooth Wear

The bottom surface of a cylindrical sample piece 6 mm in diameter and 6 mm in height was pushed onto the flat surface of a bovine tooth enamel with a load of 100 g and was turned 10000 while pouring water maintained at 37° C., so that it was worn out. The depth of wear was found by dividing the weight that is worn out by the density of the composite resin. As for the surface roughness, a mean roughness was found from ten points by using a surface roughness meter (Surfcom 570A manufactured by Tokyo Seimitsu Co.). The depth of antagonistic tooth wear was found by measuring a step on the flat surface of the bovine tooth enamel by using the surface roughness meter.

Preparation Example 1

Synthesis of Spherical Silica Particles Having a Mean Particle Diameter of 0.6 μm A tetraethyl silicate (trade name: Ethyl Silicate 28, manufactured by Colcoat Co., Ltd.) was added in an amount of 10 g with stirring to an ammoniacal alcohol solution consisting of 400 g of methyl alcohol and 100 g of 25% ammonia water in a 3-liter glass container equipped with a stirrer, and was stirred for 30 minutes and to which were then added simultaneously and dropwisely 2000 g of the tetraethyl silicate and 640 g of 25% ammonia water over a period of 4 hours while maintaining the solution temperature in the reaction vessel at 30° C. After the reaction, the solvent was distilled off from the white turbid solution in the vessel, followed by drying and firing at 1000° C. for one hour to obtain silica particles (A-1). The silica particles possessed a mean particle diameter of 0.62 μm, a truly spherical shape, and a coefficient of variation in the particle diameters of 0.05. The specific surface area was 4.5 m$^2$/g as measured by the BET method and was nearly in agreement with the surface area of 4.4 m$^2$/g that was calculated from the mean particle diameter, from which it was learned that no micro pore was present in the particles.

Preparation Examples 2 to 4

Synthesis of Spherical Silica Particles

Silica particles were obtained in the same manner as in Preparation Example 1 by using the same container as that of Preparation Example 1 but changing the composition of the initial ammoniacal alcohol solution and the amount of ammonia water to be dropped into those as shown in Table 1. The individual silica particles possessed a truly spherical shape. A mean particle diameter, a coefficient of variation in the particle diameters, a surface area calculated from the mean particle diameter and a specific surface area as measured by the BET method were as shown in Table 1.

TABLE 1

| Inorganic oxide | A-2 | A-3 | A-4 |
|---|---|---|---|
| Ammoniacal alcohol composition | | | |
| Alcohol | methanol | ethanol | ethanol |
| Alcohol amount (g) | 425 | 425 | 400 |
| Ammonia amount (g) | 75 | 75 | 100 |
| Dropped amount of ammonia water (g) | 560 | 560 | 640 |
| Mean particle diameter (μm) | 0.38 | 0.91 | 1.89 |
| Coefficient of variation | 0.08 | 0.05 | 0.03 |
| Calculated surface area (m$^2$/g) | 7.2 | 3.0 | 1.4 |
| Specific surface area (m$^2$/g) | 7.0 | 3.1 | 1.1 |

Preparation Example 5

Synthesis of Spherical Silica-zirconia Particles Having a Mean Particle Diameter of 0.5 μm 80 Grams of the tetraethyl silicate (Trade Name: Ethyl Silicate, manufactured by Colcoat Co., Ltd.) was mixed into 400 g of isobutyl alcohol (manufactured by Tonen Sekiyu Kagaku K.K.) followed by the addition of 5 g of an aqueous solution containing 0.05% of sulfuric acid. The mixture was stirred for about 1 hour at 40° C. so as to be hydrolyzed. To this solution were then mixed with stirring a solution consisting of 200 g of isobutyl alcohol in which have been dissolved 35 g of a tetrabutyl zirconate (manufactured by Nippon Soda Co., Ltd.) and a sodium methylate methanol solution (having a concentration of 28% by weight) in order to prepare a mixture solution of the tetraethyl silicate and the tetrabutyl zirconate. Next, the tetraethyl silicate was added in an amount of 4 g with stirring to an ammoniacal alcohol solution consisting of 1000 g of isobutyl alcohol and 250 g of 25% ammonia water in a 3-liter glass container equipped with a stirrer, and was stirred for 30 minutes and to which were then dropwisely added the above-mentioned mixture solution of the tetraethylsilicate and the tetrabutyl zirconate over a period of about 6 hours. During the reaction, the temperature in the reaction vessel was maintained at 40° C. After the reaction, the solvent was distilled off from the white turbid solution in the vessel, followed by drying and firing at 950° C. for one hour to obtain silica-zirconia particles (A-5). The silica-zirconia particles possessed a mean particle diameter of 0.52 μm, a truly spherical shape, and a coefficient of variation in the particle diameters of 0.13. The surface area of 4.8 m$^2$/g found from the mean particle diameter was in good agreement with the specific surface area of 4.8 m$^2$/g as measured by the BET method and no micro pore was recognized in the particles.

Preparation Example 6

Synthesis of Spherical Silica-zirconia Particles Having a Mean Particle Diameter of 0.2 μm 80 Grams of the tetraethyl silicate (Trade Name: Ethyl Silicate, manufactured by Colcoat Co., Ltd.) was mixed into 400 g of isobutyl alcohol (manufactured by Tonen Sekiyu Kagaku K.K.) followed by the addition of 5 g of an aqueous solution containing 0.05% of sulfuric acid. The mixture was stirred for about 1 hour at 40° C. so as to be hydrolyzed. To this solution were then mixed with stirring a solution consisting of 200 g of isobutyl alcohol in which have been dissolved 35 g of a tetrabutyl zirconate (manufactured by Nippon Soda Co., Ltd.) and a sodium methylate methanol solution (having a concentration of 28% by weight) in order to prepare a mixture solution of the tetraethyl silicate and the tetrabutyl zirconate. Next, the tetraethyl silicate was added in an amount of 4 g with stirring to an ammoniacal alcohol solution consisting of 1000 g of methanol and 250 g of 25% ammonia water in a 3-liter glass container equipped with a stirrer, and was stirred for 30 minutes and to which were then dropwisely added the above-mention ed mixture solution of the tetraethylsilicate and the tetrabutyl zirconate over a period of about 6 hours. During the reaction, the temperature in the reaction vessel was maintained at 40° C. After the reaction, the solvent was distilled off from the white turbid solution in the vessel, followed by drying and firing at 950° C. for one hour to obtain silica-zirconia particles (A-6). The silica-zirconia particles possessed a mean particle diameter of 0.18 μm, a truly spherical shape, and a coefficient of variation in the particle diameters of 0.17. The surface area of 13.9 m$^2$/g found from the mean particle diameter was in good agreement with the specific surface area of 14.8 m$^2$/g as measured by the BET method and no micro pore was recognized in the particles.

Preparation Example 7

Synthesis of Spherical Silica-titania Particles Having a Mean Particle Diameter of 0.25 μm 80 Grams of the tetraethyl silicate (Trade Name: Ethyl Silicate, manufactured by Colcoat Co., Ltd.) was mixed into 200 g of methanol followed by the addition of 2.5 g of an aqueous solution containing 0.04% of hydrochloric acid. The mixture was stirred for about 1 hour at 30° C. so as to be hydrolyzed. To this solution were then mixed with stirring a solution consisting of 100 g of isobutyl alcohol in which have been dissolved 10 g of a tetrabutyl titanate (manufactured by Nippon Soda Co., Ltd.) and 5 g of a sodium methylate methanol solution (having a concentration of 30% by weight) in order to prepare a mixture solution (A) of the tetraethyl silicate and the tetrabutyl titanate. Next, 5.0 g of a barium bisisopentoxide and 80 g of a tetraethyl silicate were dissolved in 700 g of methanol, and the solution was refluxed at 90° C. in a nitrogen atmosphere for 30 minutes. The temperature was decreased down to room temperature to obtain a mixture solution (B). The mixture solution (A) and the mixture solution (B) were mixed together to obtain a mixture solution (C). Next, the mixture solution (C) was dropwisely added with stirring to an ammoniacal alcohol solution consisting of 300 g of methanol and 750 g of 25% ammonia water in a 10-liter glass container equipped with a stirrer. During the reaction, the temperature in the reaction vessel was maintained at 40° C. After the reaction, the solvent was distilled off from the white turbid solution in the vessel, followed by drying and firing at 950° C. for one hour to obtain silica-titania-barium oxide particles (A-7). The silica-titania-barium oxide particles possessed a mean particle diameter of 0.25 μm and a truly spherical shape. The surface area of 10.4 m$^2$/g found from the mean particle diameter was in good agreement with the specific surface area of 10.9 m$^2$/g as measured by the BET method and no micro pore was recognized in the particles.

Preparation Example 8

Synthesis of Spherical Silica-titania Particles Having a Mean Particle Diameter of 0.08 μm 170 Grams of the tetraethyl silicate (Trade Name: Ethyl Silicate, manufactured by Colcoat Co., Ltd.) was mixed into 400 g of methanol followed by the addition of 5 g of an aqueous solution containing 0.04% of hydrochloric acid. The mixture was stirred for about 1 hour at 30° C. so as to be hydrolyzed. To this solution were then mixed with stirring a solution consisting of 200 g of isobutyl alcohol in which have been dissolved 20 g of a tetrabutyl titanate (manufactured by Nippon Soda Co., Ltd.) and 10 g of a sodium methylate methanol solution (having a concentration of 28% by weight) in order to prepare a mixture solution of the tetraethyl silicate and the tetrabutyl titanate. Next, 2 g of the tetraethyl silicate was added with stirring into an ammoniacal alcohol solution consisting of 1000 g of methanol and 250 g of 25% ammonia water in a 3-liter glass container equipped with a stirrer, and the mixture was stirred for 30 minutes, followed by the dropwise addition of the mixture solution of the tetraethyl silicate and the tetrabutyl titanate over a period of about 5 hours. During the reaction, the temperature in the reaction vessel was maintained at 40° C. After the reaction, the solvent was removed by distillation from the white turbid solution in the vessel, followed by drying and firing at 950° C. for one hour to obtain silica-titania particles (B-1). The silica-titania particles possessed a mean particle diameter of 0.077 μm and a truly spherical shape. The surface area of 33.9 m$^2$/g found from the mean particle diameter was in good agreement with the specific surface area of 32.5 m$^2$/g as measured by the BET method and no micro pore was recognized in the particles.

Preparation Example 9

Synthesis of Spherical Silica-zirconia Particles Having a Mean Particle Diameter of 0.06 μm Silica-zirconia particles (B-2) were obtained in the same manner as in Preparation Example 6 but without adding tetraethyl silicate into the ammoniacal alcohol solution which consists of 1000 g of methanol and 200 g of 25% ammonia water in a 3-liter glass container equipped with a stirrer but, instead, dropwisely adding thereto a mixture solution of the tetraethyl silicate and the tetrabutyl zirconate over a period of about 3 hours. The silica-zirconia particles possessed a mean particle diameter of 0.058 μm and a truly spherical shape. The surface area of 43.1 m$^2$/g found from the mean particle diameter was in good agreement with the specific surface area of 47.4 m$^2$/g measured by the BET method and no micro pore was recognized in the particles.

Inorganic oxides and their abbreviations in addition to those used in the above-mentioned Preparation Examples were as follows:

B-3: Fine powdery silica, REOLOSIL QS102 manufactured by Tokuyama Co., specific surface area: 200 m$^2$/g (mean particle diameter: not larger than 0.02 μm).

Fine magnesia particles: UC-999 manufactured by Ube Chemical Industries Co., Ltd., mean particle diameter: 0.028 μm.

Fine alumina particles: High-purity alumina XA-10 manufactured by Nikkeikako Co., specific surface area: 105 m$^2$/g (mean particle diameter: not larger than 0.04 μm).

Example 1

80 Grams of spherical silica particles having a mean particle diameter of 0.6 μm and 20 g of spherical silica-titania particles having a mean particle diameter of 0.08 μm were introduced into 400 g of pure water solvent, and were dispersed by using an emulsifying/dispersing nanomizer that gives shock under super high pressure of 60 MPa. After the surfaces were treated with a γ-methacryloxypropyltrimethoxysilane, the solvent was distilled off, followed by drying to obtain an inorganic composition. As a result of measuring the distribution of pore diameters of the inorganic composition, it was learned that the volume of micro pores due to strongly aggregated particles having pore diameters of not smaller than 0.08 μm was 0.1 cc per gram of the inorganic composition, and the volume of micro pores due to strongly aggregated particles having pore diameters over a range of from 0.008 to 0.064 μm was 0.03 cc per gram of the inorganic composition. At the same time, properties of the powder were measured by the dry tapping, and it was found that the flow index a was 0.35, the adhesive force index 1/b was 9.5, and the final tapping bulk density was 1.33 g/cc.

To the surface-treated product was gradually added a matrix monomer bis-GMA/3G (weight ratio of 60/40) which is a radical polymerizable monomer in which have been dissolved camphorquinone and ethyldimethylaminobenzoic ester as a polymerization initiator and a reducing agent each in an amount of 0.5% until a limit paste-like state is reached, thereby to obtain a composite composition. The content of the inorganic filler (% by weight) at this moment is regarded to be an inorganic filling ratio. The inorganic filling ratio was 85.5% by weight. The paste was then polymerized and cured by being irradiated with light to evaluate the properties. As a result, the compressive strength was 525 MPa, three-point bending strength was 222 MPa, depth of wear was 8.4 μm, surface roughness was 0.49 μm, and the depth of antagonistic tooth wear was 1.6 μm.

Examples 2 to 13

Inorganic compositions were obtained in the same manner as in Example 1 but changing the compositions of inorganic oxides to be blended into those as shown in Table 2. From the results of measurement of pore diameter distributions based upon the mercury porosimetry, volumes of micro pores due to strongly aggregated particles having pore diameters of not smaller than 0.08 μm, and volumes of micro pores due to strongly aggregated particles having pore diameters over a range of 0.1 to 0.8 times as large as the mean particle diameters of the inorganic oxide fine particles (B) denoted by B-1 and B-2, were found as shown in Table 2. For reference, Table 2 also shows flow index, adhesive force index and final tapping bulk density which are properties of dry powders by tapping.

The measured example of FIG. 1 described in this specification is that of the inorganic composition (C) of Example 11.

Figure 2:
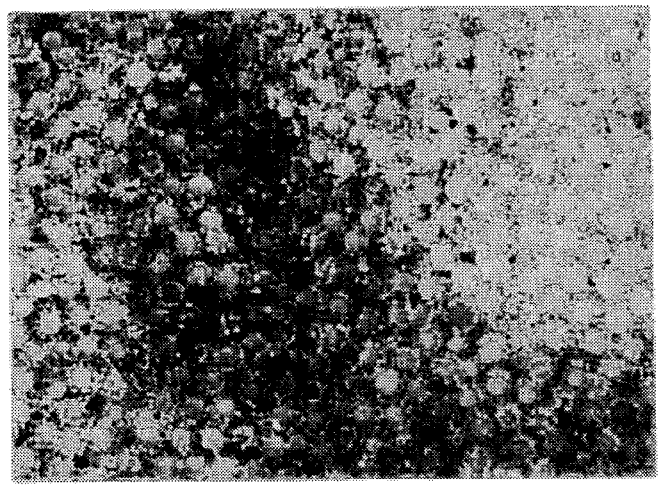
FIG. 2 is a photograph illustrating particle structure of an inorganic composition used in Example 8.
Figure 3:
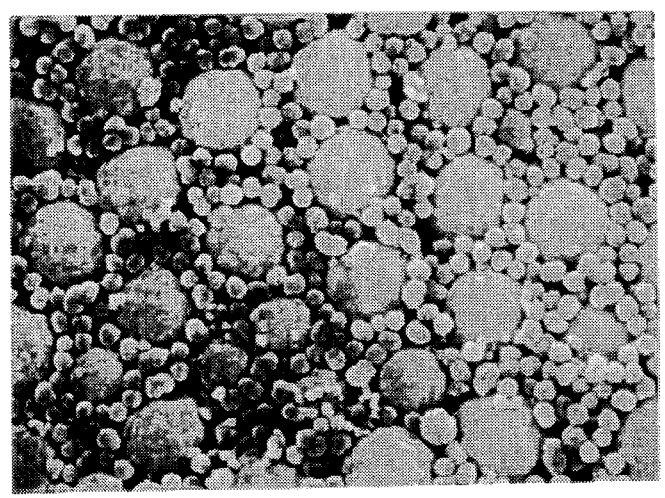
FIG. 3 is a photograph illustrating particle structure of an inorganic composition used in Example 8.
Figure 4:
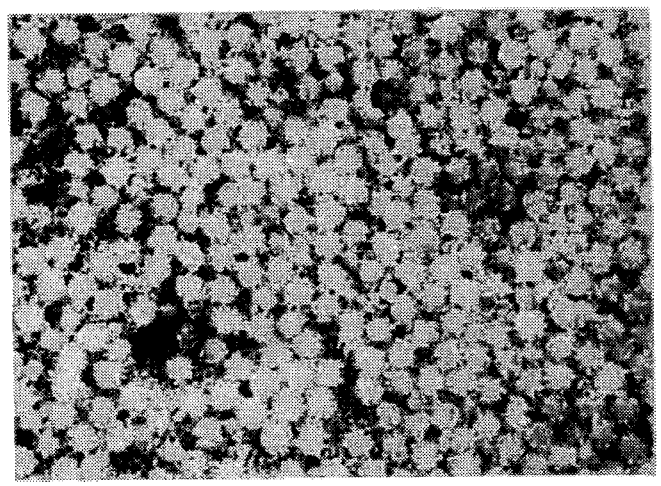
FIG. 4 is a photograph illustrating particle structure of an inorganic composition used in Example 12.
Figure 5:
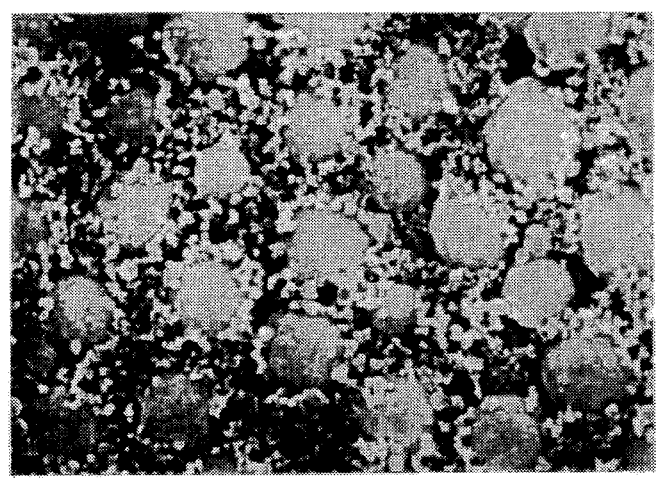
FIG. 5 is a photograph illustrating particle structure of an inorganic composition used in Example 12.

FIGS. 2 and 3 are SEM photographs of inorganic compositions obtained in Example 8, and FIGS. 4 and 5 are SEM photographs of inorganic compositions obtained in Example 12. It will be observed in all of these photographs that the particles are well dispersed and have high bulk densities.

In the same manner as in Example 1, furthermore, the inorganic fillers and the radical-polymerizable monomer were mixed together to prepare pastes which were then polymerized and cured by being irradiated with light to evaluate the properties. The inorganic filling ratios, compressive strengths, three-point bending strengths, depths of wear, surface roughnesses and depths of antagonistic tooth wear were as shown in Table 3.

TABLE 2

| Example | Inorganic composition (% by weight) | | | | | | | Volume of micro pores due to strongly aggregated particles (cc/g) | | Flow index | Adhesive force index | Final tapping density |
| | A-1 | A-2 | A-3 | A-5 | A-6 | B-1 | B-3 | A | B | a | 1/b | (g/cc) |
| --- | --- | --- | --- | --- | --- | --- | --- | --- | --- | --- | --- | --- |
| 2 | 90 | | | | | 10 | | 0.01 | 0.04 | 0.32 | 8.8 | 1.25 |
| 3 | 70 | | | | | 30 | | 0.02 | 0.05 | 0.36 | 9.8 | 1.27 |
| 4 | | 95 | | | | | 5 | 0.01 | 0.12 | 0.35 | 8.2 | 1.15 |
| 5 | | 90 | | | | 10 | | 0.01 | 0.12 | 0.36 | 9.5 | 1.06 |
| 6 | | | 60 | | | 40 | | 0.06 | 0.06 | 0.32 | 9.0 | 1.20 |
| 7 | | | | 90 | | 10 | | 0.01 | 0.05 | 0.29 | 8.5 | 1.40 |
| 8 | | | | 80 | | 20 | | 0.01 | 0.03 | 0.32 | 8.5 | 1.28 |
| 9 | | | | 70 | | 30 | | 0.02 | 0.07 | 0.35 | 8.8 | 1.19 |
| 10 | | | | 70 | 20 | 10 | | 0.05 | 0.04 | 0.37 | 9.0 | 1.13 |
| 11 | | | | 80 | | 10 | 10 | 0.06 | 0.17 | 0.36 | 9.4 | 1.24 |
| 12 | | | | 80 | | | 20 | 0.06 | 0.20 | 0.37 | 8.7 | 1.06 |
| 13 | | | | | 80 | | 20 | 0.03 | 0.18 | 0.37 | 9.7 | 1.02 |

Volumes A, B of micro pores due to strongly aggregated particles are as follows:
A: Volume of micro pores due to strongly aggregated particles having pore diameters of not smaller than 0.08 μm.
B: Volume of micro pores due to strongly aggregated particles having pore diameters over a range of 0.1 to 0.8 times as large as the mean particle diameters of inorganic oxide fine particles (B) denoted by B-1 and B-2.

TABLE 3

| Example | Inorganic filling rate (% by wt.) | Compressive strength (MPa) | 3-point bending (MPa) | Depth of wear (μm) | Surface roughness (μm) | Depth of antagonistic tooth wear (μm) |
| --- | --- | --- | --- | --- | --- | --- |
| 2 | 83.8 | 495 | 176 | 9.1 | 0.48 | 1.8 |
| 3 | 84.0 | 516 | 188 | 7.5 | 0.44 | 1.8 |
| 4 | 80.3 | 470 | 160 | 6.5 | 0.31 | 1.2 |
| 5 | 81.7 | 458 | 144 | 6.8 | 0.29 | 1.4 |
| 6 | 82.1 | 539 | 230 | 11.2 | 0.70 | 3.2 |
| 7 | 84.5 | 511 | 191 | 5.1 | 0.48 | 2.6 |
| 8 | 86.0 | 520 | 202 | 4.6 | 0.48 | 1.7 |
| 9 | 84.3 | 505 | 197 | 4.8 | 0.47 | 1.5 |
| 10 | 83.2 | 504 | 183 | 5.3 | 0.41 | 1.7 |
| 11 | 84.0 | 467 | 195 | 4.9 | 0.42 | 1.6 |
| 12 | 81.9 | 450 | 125 | 5.5 | 0.26 | 1.1 |
| 13 | 80.4 | 445 | 130 | 6.1 | 0.09 | 0.4 |

Example 14

The procedure was carried out in the same manner as in Example 1 but changing the matrix monomer into D-2.6E/3G (weight ratio of 70/30). The inorganic filling ratio was 87.1% by weight, compressive strength was 509 MPa, three-point bending strength was 200 MPa, depth of wear was 7.7 μm, surface roughness was 0.46 μm, and depth of antagonistic tooth wear was 1.4 μm.

Example 15

The procedure was carried out in the same manner as in Example 8 but changing the matrix monomer into tetramethylolmethane trimethacrylate/3G (weight ratio of 70/30). The inorganic filling ratio was 86.8% by weight, compressive strength was 510 MPa, three-point bending strength was 185 MPa, depth of wear was 4.1 μm, surface roughness was 0.41 μm, and depth of antagonistic tooth wear was 1.4 μm.

Example 16

The procedure was carried out in the same manner as in Example 8 but using a homogenizer to mix and disperse the inorganic oxides. The volume of micro pores due to strongly aggregated particles having pore diameters of not smaller than 0.08 μm was 0.03 cc/g and the volume of micro pores due to strongly aggregated particles having pore diameters of 0.008 to 0.064 μm was 0.04 cc/g. The flow index was 0.32, adhesive force index was 8.9, final tapping bulk density was 1.30 g/cc, inorganic filling ratio was 86.4% by weight, compressive strength was 485 MPa, three-point bending strength was 155 MPa, depth of wear was 3.8 μm, surface roughness was 0.39 μm and depth of antagonistic tooth wear was 1.5 μm.

Example 17

The procedure was carried out in the same manner as in Example 1 but changing the inorganic oxide particles A-5 into inorganic oxide particles A-7 and changing the inorganic oxide fine particles B-1 into magnesia fine particles. The volume of micro pores due to strongly aggregated particles having pore diameters of not smaller than 0.08 μm was 0.04 cc/g, the volume of micro pores due to aggregated particles having pore diameters of 0.003 to 0.022 μm was 0.08 cc/g, the inorganic filling ratio was 81.6% by weight, compressive strength was 426 MPa, three-point bending strength was 149 MPa, depth of wear was 5.5 μm, surface roughness was 0.20 μm and depth of antagonistic tooth wear was 0.4 μm.

Example 18

The procedure was carried out in the same manner as in Example 1 but changing the pressure for mixing and dispersing the particles by the nanomizer into 120 MPa. The volume of micro pores due to strongly aggregated particles having pore diameters of not smaller than 0.08 μm was not observed. The volume of micro pores due to aggregated particles having pore diameters of 0.008 to 0.064 μm was 0.02 cc/g, the inorganic filling ratio was 85.4% by weight, compressive strength was 530 MPa, three-point bending strength was 247 MPa, depth of wear was 7.8 μm, surface roughness was 0.50 μm and depth of antagonistic tooth wear was 1.8 μm. There was obtained a composite composition having further improved mechanical strength and excellent surface smoothness.

Example 19

The procedure was carried out in the same manner as in Example 8 but changing the inorganic oxide fine particles B-1 into inorganic oxide fine particles B-2 and changing pressure for mixing and dispersing the particles by the nanomizer into 120 MPa. The volume of micro pores due to strongly aggregated particles having pore diameters of not smaller than 0.08 μm was 0.01 cc/g, the volume of micro pores due to aggregated particles having pore diameters of 0.006 to 0.048 μm was 0.02 cc/g, the inorganic filling rate was 85.8% by weight, compressive strength was 535 MPa, three-point bending strength was 238 MPa, depth of wear was 4.6 μm, surface roughness was 0.43 μm and depth of antagonistic tooth wear was 1.5 μm.

Example 20

The procedure was carried out in the same manner as in Example 8 but changing the inorganic oxide fine particles B-1 into alumina fine particles and changing pressure for mixing and dispersing the particles by the nanomizer into 120 MPa. The volume of micro pores due to strongly aggregated particles having pore diameters of not smaller than 0.08 μm was 0.02 cc/g, but the volume of micro pores due to aggregated particles having pore diameters of 0.001 to 0.008 μm was not detected due to limitation in the measurement, the inorganic filling rate was 83.6% by weight, compressive strength was 454 MPa, three-point bending strength was 138 MPa, depth of wear was 5.0 μm, surface roughness was 0.45 μm and depth of antagonistic tooth wear was 2.0 μm.

Comparative Example 1

A composite composition was obtained in the same manner as in Example 1 but using the inorganic oxide A-4 instead of the inorganic oxide A-1. Table 4 shows properties of the obtained inorganic composition and Table 5 shows properties of the composite composition and the cured product thereof. Though excellent mechanical strength was obtained, smooth surface was not obtained. Depth of antagonistic tooth wear was great, too.

Comparative Example 2

The procedure was carried out in the same manner as in Example 1 but using the inorganic oxide B-1 instead of the inorganic oxide A-1 and using the inorganic oxide B-2 instead of the inorganic oxide B-1. Table 4 shows properties of the obtained inorganic composition and Table 5 shows properties of the composite composition and the cured product thereof. Smooth surfaces were obtained and antagonistic tooth wear was small. The mechanical strength, however, was poor.

Comparative Example 3

The procedure was carried out in the same manner as in Example 1 but using the inorganic oxide A-5 instead of the inorganic oxide A-1 and using the inorganic oxide A-6 instead of the inorganic oxide B-1. Table 4 shows properties of the obtained inorganic composition and Table 5 shows properties of the composite composition and of the cured product thereof. Surface smoothness and wear resistance of antagonistic tooth were good, but the mechanical strength was poor.

Comparative Example 4

The procedure was carried out in the same manner as in Example 8 but changing the blending ratio of inorganic oxide A-5 and inorganic oxide B-1 into 50:50. Table 4 shows properties of the obtained inorganic composition and Table 5 shows properties of the composite composition and of the cured product thereof. Surface smoothness and wear resistance of antagonistic tooth were good, but the mechanical strength was poor.

Comparative Example 5

Figure 6:
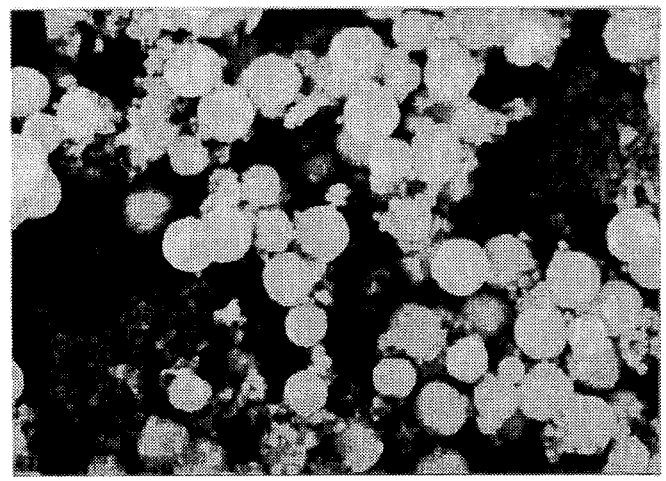
FIG. 6 is a photograph illustrating particle structure of an inorganic composition used in Comparative Example 5.

The procedure was carried out in the same manner as in Example 8 but mixing and dispersing the inorganic oxide particles by using a ball mill having a capacity of 2 liters for one hour. Table 4 shows properties of the obtained inorganic composition and FIG. 6 is a photograph obtained by using an SEM. Volumes of micro pores due to aggregated particles were large, and large voids were observed through the SEM in the aggregation of particles and among the particles. Table 5 shows properties of the composite composition and of the cured product thereof. The mechanical strength was poor and, in particular, the three-point bending strength was poor.

TABLE 4

| Comparative Example | Inorganic composition (% by weight) | | | | | Volume of micro pores due to strongly aggregated particles (cc/g) | | Flow index | Adhesive force index | Final tapping density |
|---|---|---|---|---|---|---|---|---|---|---|
| | A-4 | A-5 | A-6 | B-1 | B-3 | A | B | a | 1/b | (g/cc) |
| 1 | 80 | | | 20 | | 0.01 | 0.22 | 0.31 | 8.2 | 1.51 |
| 2 | | | | 80 | 20 | 0.07 | 0.30 | 0.38 | 12 | 0.83 |
| 3 | | 80 | 20 | | | 0.03 | 0.03 | 0.34 | 9.1 | 1.16 |
| 4 | | 50 | | 50 | | 0.11 | 0.19 | 0.36 | 9.8 | 1.04 |
| 5 | | 80 | | 20 | | 0.2 | 0.31 | 0.39 | 19 | 0.79 |

Volumes A, B of micro pores due to strongly aggregated particles are as follows:
A: Volume of micro pores due to strongly aggregated particles having pore diameters of not smaller than 0.08 μm.
B: Volume of micro pores due to strongly aggregated particles having pore diameters over a range of 0.1 to 0.8 times as large as the mean particle diameters of inorganic oxide fine particles (B) denoted by B-1 and B-2.

TABLE 5

| Comparative Example | Inorganic filling rate (% by wt.) | Compressive strength (MPa) | 3-point bending (MPa) | Depth of wear (μm) | Surface roughness (μm) | Depth of antagonistic tooth wear (μm) |
|---|---|---|---|---|---|---|
| 1 | 88.5 | 530 | 234 | 2.1 | 1.30 | 11.0 |
| 2 | 77.2 | 395 | 76 | 6.5 | 0.06 | 0.3 |
| 3 | 78.7 | 470 | 88 | 7.7 | 0.44 | 1.6 |
| 4 | 79.0 | 438 | 88 | 5.6 | 0.42 | 1.3 |
| 5 | 83.7 | 415 | 58 | 7.2 | 0.48 | 1.6 |

Comparative Example 6

The procedure was carried out in the same manner as in Example 8 but using a composite oxide (Glass-Powder 8235 manufactured by Schott glaswerke) of an indeterminate shape having a particle diameter of 0.79 μm instead of using the inorganic oxide A-5. The obtained inorganic composition possessed a volume of micro pores due to strongly aggregated particles of not smaller than 0.08 μm of 0.06 cc/g, the composite composition possessed an inorganic filling ratio of 73.5% by weight, and the cured product thereof possessed inferior mechanical strength exhibiting a compressive strength of 310 MPa and a three-point bending strength of 48 MPa.

We claim:

1. An inorganic composition (C) which comprises (A) 60 to 99% by weight of spherical inorganic oxide particles having a mean particle diameter greater than 0.1 µm but not greater than 1 µm, and (B) 40 to 1% by weight of inorganic oxide fine particles having a mean particle diameter not greater than 0.1 µm, wherein a volume of micro pores due to strongly aggregated particles having pore diameters not smaller than 0.08 µm is not greater than 0.1 cc per gram of the inorganic composition (C).

2. An inorganic composition (C) according to claim 1, wherein a volume of micro pores due to strongly aggregated particles having pore diameters over a range of from 0.1 to 0.8 times as large as the mean particle diameter of the inorganic oxide fine particles (B) is not greater than 0.1 cc per gram of the inorganic composition (C).

3. An inorganic composition (C) according to claim 1, wherein said spherical inorganic oxide particles comprise a siliciferous compound or an aluminiferous compound.

4. An inorganic composition (C) according to claim 3, wherein said siliciferous compound comprises amorphous silica, silica-zirconia, silica-titania, silica-titania-barium oxide or quartz.

5. An inorganic composition (C) according to claim 3, wherein said aluminiferous compound comprises alumina.

6. An inorganic composition (C) according to claim 1, wherein said spherical inorganic oxide particles (A) have a particle diameter distribution with a coefficient of variation defined by the following formula $$\text{Coefficient of variation} = \frac{\sigma_{n-1}}{\overline{Y}}$$

wherein, $$\overline{Y} = \frac{\sum_{i=1}^{n} X_i}{n} \quad \text{(number average diameter)}$$

$$\sigma_{n-1} = \sqrt{\frac{\sum_{i=1}^{n} (X_i - \overline{Y})^2}{n-1}}$$

where, n: number of particles observed, $X_i$: diameter of i-th particle, wherein said coefficient of variation is not larger than 0.3.

7. An inorganic composition (C) according to claim 1, wherein said inorganic oxide fine particles (B) comprise an oxide of an element of the Group IIIA, the Group IVA or the Group IVB of the periodic table.

8. An inorganic composition (C) according to claim 1, wherein said inorganic oxide fine particles (B) comprise fumed silica, fumed alumina, fumed zirconia, fumed titania, amorphous silica, silica-zirconia, silica-titania, silica-titania-barium oxide, quartz or alumina.

9. An inorganic composition (C) according to claim 1, comprising 70 to 90% by weight of spherical inorganic oxide particles (A) and 30 to 10% by weight of inorganic oxide fine particles (B).

10. An inorganic composition (C) according to claim 1, having substantially a dispersion structure that is shown in an electron microphotograph of FIG. 3.

11. An inorganic composition (C) according to claim 1, wherein the surfaces of the inorganic composition are treated with a silane coupling agent.

12. An inorganic composition (C) according to claim 2, wherein the surfaces of the inorganic composition are treated with a silane coupling agent.

13. A filler comprising the inorganic composition of claim 1.

14. A composite composition useful for dental applications comprising 50 to 95% by weight of the inorganic composition of claim 1 or said inorganic composition treated with a silane coupling agent, 50 to 5% by weight of a radical-polymerizable monomer, and a catalytic amount of a radical polymerization catalyst.

15. A composite composition useful for dental applications comprising 50 to 95% by weight of the inorganic composition of claim 2 or said inorganic composition treated with a silane coupling agent, 50 to 5% by weight of a radical-polymerizable monomer, and a catalytic amount of a radical polymerization catalyst.

* * * * *